(12) United States Patent
Howe et al.

(10) Patent No.: US 7,483,457 B2
(45) Date of Patent: Jan. 27, 2009

(54) LASER SYSTEM

(75) Inventors: Christopher Andrew Howe, Ely (GB); Edmund Hugh Emile St. Paer-Gotch, Wickford (GB)

(73) Assignee: AngioDynamics, Inc., Queensbury, NY (US)

( * ) Notice: Subject to any disclaimer, the term of this patent is extended or adjusted under 35 U.S.C. 154(b) by 605 days.

(21) Appl. No.: 10/521,383

(22) PCT Filed: Jul. 25, 2003

(86) PCT No.: PCT/GB03/03205

§ 371 (c)(1),
(2), (4) Date: Sep. 14, 2005

(87) PCT Pub. No.: WO2004/010885

PCT Pub. Date: Feb. 5, 2004

(65) Prior Publication Data

US 2006/0089629 A1  Apr. 27, 2006

(30) Foreign Application Priority Data

Jul. 25, 2002 (GB) ................................. 0217273.2

(51) Int. Cl.
*H01S 3/30* (2006.01)
*H01S 3/00* (2006.01)
*A61B 18/22* (2006.01)

(52) U.S. Cl. ....................... 372/38.02; 372/8; 606/16

(58) Field of Classification Search ................. 372/8, 372/38.1, 38.01, 38.02; 606/10, 16, 33
See application file for complete search history.

(56) References Cited

U.S. PATENT DOCUMENTS

| 5,445,146 | A | 8/1995 | Bellinger |
| 5,959,531 | A | 9/1999 | Gallagher, III et al. |
| 6,100,804 | A | 8/2000 | Brady et al. |
| 6,293,467 | B1 | 9/2001 | Reddersen et al. |
| 2002/0034365 | A1 | 3/2002 | Vogelsang |

FOREIGN PATENT DOCUMENTS

| EP | 0408160 A | 1/1991 |
| EP | 0473987 A | 3/1992 |
| EP | 0867151 A | 9/1998 |
| JP | 11295565 | 10/1999 |
| WO | WO 03/030408 A | 4/2003 |

*Primary Examiner*—Armando Rodriguez
(74) *Attorney, Agent, or Firm*—Abelman Frayne & Schwab; Harry K. Ahn

(57) ABSTRACT

A laser system is disclosed comprising a laser device for emitting laser radiation and an optical fiber adapted to connect, in use, to the laser device for delivering the laser radiation. The optical fiber contains a label, such as an RF identification tag, a barcode or a color code. The laser device interrogates the optical fiber and receives information back from the optical fiber. If the usage of the optical fiber has exceeded safety limits then the laser device may be prevented from operating. The laser device on receiving information from the optical fiber may also be configured to deliver laser radiation having a specific power, pulse width, pulse interval and treatment duration.

33 Claims, 1 Drawing Sheet

LASER SYSTEM

RELATED APPLICATIONS

This application is a national stage filing under 35 U.S.C. § 371 of International Application No. PCT/GB03/003205, filed Jul. 25, 2003, which is an international application of and claims priority to United Kingdom Application No. GB 0217273.2, filed Jul. 25, 2002.

BACKGROUND OF THE INVENTION

1. Field of Invention

The present invention relates to a laser system and a method of operating a laser system.

2. Discussion of Related Art

Medical lasers are used in certain medical procedures to administer thermal or other energy to a patient with beneficial effects. For example, energy can be used to detect or treat a tumour or a region of the body, or to destroy or denature diseased or malfunctioning body tissue. U.S. Pat. No. 6,095,149 describes, for example, the treatment of invertebral disc abnormalities with thermal energy. Other forms of medical treatment utilise laser energy such as endovenous laser treatment (EVLT) wherein laser energy is delivered to the inner wall of a vein.

A known laser system comprises a laser device for emitting laser radiation and an optical fibre for directing the laser radiation to the required location. The laser system may be used for a variety of different purposes and optical fibres for use with the laser device may be provided with a standard connector for attachment to the laser device.

Optical fibres used in conjunction with a laser device may, in certain circumstances, have a relatively limited lifetime. For example, the lifetime of an optical fibre may be limited due to hygiene requirements in medical applications. An optical fibre may additionally/alternatively also have a limited lifetime before it becomes susceptible to damage.

A laser device may have been initially calibrated with a new optical fibre to deliver a certain intensity laser beam. However, if the optical fibre is reused a number of times then the presence of dirt etc. on the optical fibre may result in a lower than desired intensity laser beam being delivered which, for example in medical applications, could render the intended medical treatment ineffective.

In some applications optical fibres may only be intended for single use and should be disposed of thereafterwards for health and safety reasons. EP 0473987 discloses a method and apparatus for optoelectrical recognition of disposable medical applicators connected to a laser.

SUMMARY OF INVENTION

According to an aspect of the present invention there is provided a laser system comprising:

a laser device for emitting laser radiation; and a delivery device adapted to connect, in use, to the laser device for delivering the laser radiation;

wherein, in use, the laser device receives information from the delivery device.

An advantage of the preferred embodiment is that an operator can be certain that a correct, safe and effective optical fibre or other delivery device has been attached to the laser device and that the optical fibre or other delivery device is suitable for the intended use. This may be particularly important in medical applications.

The delivery device is preferably an optical fibre and the laser device preferably includes a detector for detecting the connection of the delivery device. The laser device preferably interrogates the delivery device after detecting the connection. The laser device preferably interrogates the delivery device or optical fibre in a contactless manner.

Information is preferably encoded, embedded within or otherwise stored with the delivery device and may indicate the type, usage, state, age, intended use and/or function of the delivery device.

According to a preferred embodiment the delivery device comprises an AC or RF identification tag or transponder. The identification tag may be either a read only device or in an alternative embodiment a read/write device.

The laser device preferably comprises an AC or RF identification reader for reading the AC or RF identification tag or transponder. In use, the delivery device preferably transmits or returns a signal to the AC or RF identification reader.

According to a preferred embodiment the delivery device receives, in use, a power pulse. The delivery device preferably receives AC or RF energy, stores the energy and then transmits back to the laser device data or information using the stored energy.

According to a less preferred embodiment the delivery device may comprise a barcode and the laser device may comprise a barcode reader.

According to another less preferred embodiment the delivery device may comprise a colour identification tag and the laser device may identify the colour identification tag.

The laser device preferably comprises a SMA-905 connector for receiving an optical fibre.

According to a preferred embodiment in a mode of operation the laser device prevents operation with the delivery device upon receiving information from the delivery device. In a mode of operation the laser device may prevent operation with the delivery device if the laser device does not receive any information from the delivery device. The laser device may also prevent operation if a conventional delivery device known per se, for example a known delivery device which does not transmit information to the laser device, is connected to the laser device.

The laser device may in a mode of operation prevent operation with the delivery device if the laser device receives information from the delivery device and wherein the information indicates a predetermined parameter is unsuitable or has been exceeded. The parameter may, for example, indicate the usage, sterility, type and/or expiry date of the delivery device. If the laser device does disable or limit operation with a delivery device then in a mode of operation the laser device may be enabled and/or disabled remotely, for example via a telephone link, a serial interface, via the internet or other means.

The laser device may be provided with a visual display adapted to provide the user with information received from the delivery device.

According to a preferred embodiment in a mode of operation the laser device receives information from the delivery device and sets the power and/or pulse width and/or interval between pulses and/or duration of laser radiation to be transmitted to the delivery device and hence delivered by the delivery device. Advantageously, this enables the laser device to be safely operated without requiring a skilled technician to control the operation of the laser device.

According to another aspect of the present invention there is provided an optical fibre assembly comprising an AC or RF identification tag or transponder.

According to another aspect of the present invention there is provided a laser device comprising a reader for reading an AC or RF identification tag or transponder on an optical fibre assembly.

According to another aspect of the present invention there is provided a laser system comprising:

an optical fibre assembly comprising an AC or RF identification tag or transponder; and a laser device comprising a reader for reading the AC or RF identification tag or transponder.

According to another aspect of the present invention there is provided an optical fibre comprising a barcode.

According to another aspect of the present invention there is provided a laser device comprising a barcode reader for reading a barcode on an optical fibre.

According to another aspect of the present invention there is provided a laser system comprising:

an optical fibre comprising a barcode; and a laser device comprising a barcode reader for reading the barcode.

According to another aspect of the present invention there is provided a laser system comprising:

a laser device for emitting laser radiation; and a delivery device adapted to connect, in use, to the laser device for delivering the laser radiation, the delivery device comprising a read/write device for storing information;

wherein, in use, the laser device updates the information on the read/write device.

Preferably, the laser system in accordance with any aspect of the present invention comprises a medical laser system.

According to another aspect of the present invention there is provided a medical laser system comprising:

a laser device for emitting laser radiation; and a delivery device adapted to connect, in use, to the laser device for delivering the laser radiation;

wherein, in use, the laser device receives information from the delivery device.

According to another aspect of the present invention there is provided a method of operating a laser system comprising the steps of:

providing a laser device; and connecting a delivery device to the laser device;

wherein said laser device receives information from the delivery device.

According to another aspect of the present invention there is provided a method of operating a laser system comprising providing a laser device and a delivery device wherein the laser device interrogates the delivery device. Preferably, the laser device detects the attachment of the delivery device prior to interrogating the delivery device.

According to another aspect of the present invention there is provided a method of operating a laser system comprising the steps of:

providing a laser device; and attaching a delivery device to the laser device;

wherein the laser device detects the attachment of the delivery device and interrogates the delivery device upon detection of the attachment of the delivery device.

Preferably, the method of any aspect of the present invention further comprises the laser device enabling operation of the laser system upon receiving information from the delivery device.

The laser device preferably receives information from the delivery device and displays the information for the user. The information received by the laser device from the delivery device may preferably indicate the usage, sterility, type or expiry date of the delivery device.

A method of operating a laser system in accordance with any aspect of the present invention may preferably further include in a mode of operation the laser device being enabled and/or disabled remotely.

According to another aspect of the present invention there is provided a method of operating a laser system comprising the steps of:

providing a laser device;

attaching a delivery device to a laser device; and transmitting a power pulse to the delivery device;

wherein the delivery device receives the pulse, stores the pulse and transmits data to the laser device using the pulse. The pulse is preferably a pulse of AC or RF energy.

Preferably, the laser device may receive information from the delivery device and configure the operation of the laser device.

BRIEF DESCRIPTION OF DRAWINGS

Various embodiments of the present invention will now be described, by way of example only, and with reference to the accompanying drawing in which.

DETAILED DESCRIPTION

Figure 1:
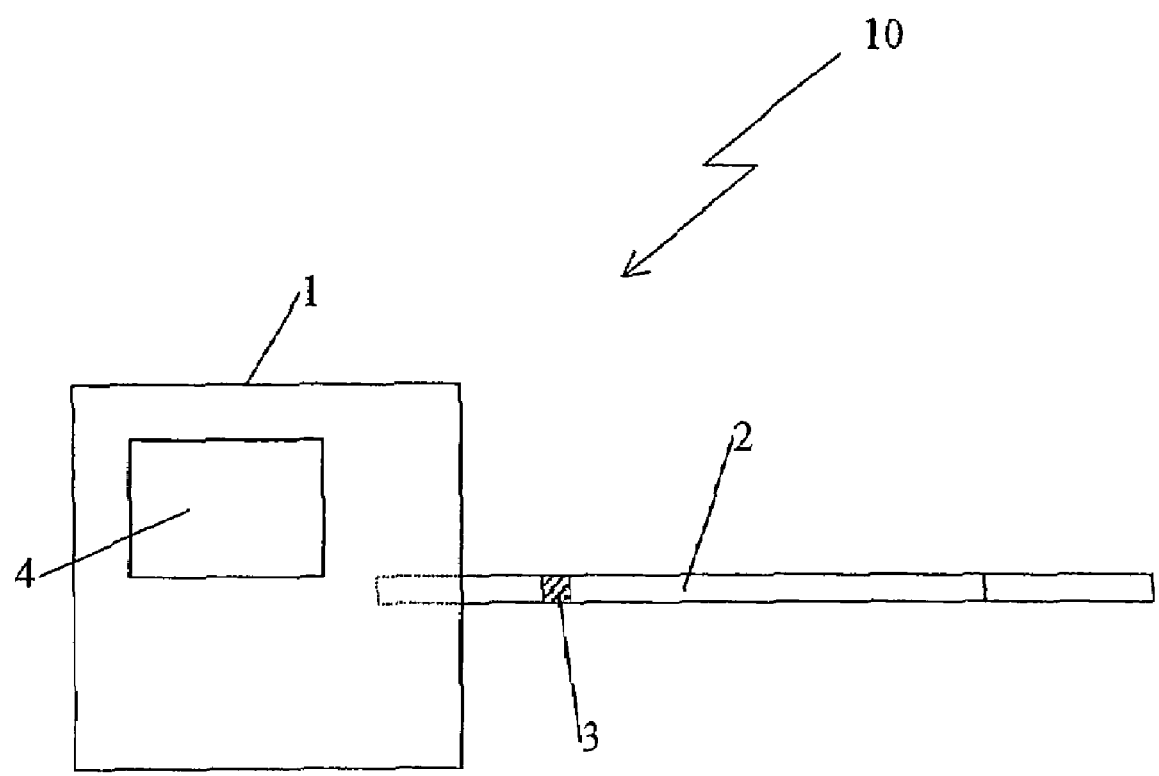
FIG. 1 shows a laser system according to the preferred embodiment.

A preferred embodiment of the present invention will now be described with reference to FIG. 1. A laser system 10 is shown comprising a laser device 1 for emitting laser radiation and a delivery device 2 adapted and arranged to be connected to the laser device 1.

According to the preferred embodiment, the laser device 1 is an 810 nm diode laser manufactured by DIOMED, Ltd., United Kingdom and the delivery device 2 is an optical fibre. The delivery device 2 may be connected to the laser device 1 using any suitable connector/fibre terminator such as a standard sub-miniature A (SMA) connector. Alternatively, according to a less preferred embodiment, the delivery device may comprise a mirror based delivery system.

The delivery device 2 is preferably fully compatible with existing systems. For example, the delivery device 2 is preferably suitable for interfacing with various accessories such as EVLT sheathes, spot handpieces and ENT accessories.

Information from the delivery device 2 is received by the laser device 1. Receiving information from the delivery device 2 preferably does not require any additional connection between the laser device 1 and the delivery device 2, and a contactless method of receiving information from the delivery device 2 is particularly preferred. According to the preferred embodiment an AC or RF tag or transponder 3 is embedded within or provided on the delivery device 2. The data or information received by the laser device 1 from the delivery device 2 is preferably pre-assigned to the delivery device 2 during manufacture.

A reader for receiving information from the delivery device 2 is preferably provided within the laser device 1. The reader may collect data or information which is then transferred through standard interfaces to the control of the laser device 1.

The reader provided within the laser device 1 may read an RF or AC identification tag or transponder 3 provided on the delivery device 2. The reader preferably comprises an antenna, a transceiver and a processor. The RF or AC identification tag or is transponder 3 preferably comprises an antenna and an integrated circuit or silicon chip. The RF or AC identification tag or transponder 3 may be encapsulated in glass or plastic which may then be attached to the delivery device 2.

In an embodiment the identification tag or transponder 3 may be a passive system which remains in an OFF state until activated by a signal from the reader. Preferably, the identification tag or transponder 3 is of the type which does not require an internal power source such as a battery.

According to a preferred embodiment the AC or RF identification tag or transponder 3 is embedded within a moulding attached to the delivery device 2 e.g. optical fibre. The moulding is preferably attached to the delivery device 2 or optical fibre approximately 5 cm from a connector which is used to connect the optical fibre 2 to the laser device 1. Thus, when the delivery device 2 or optical fibre is attached to the laser device 1 the identification tag or transponder 3 remains external to the laser device 1.

According to other embodiments the delivery device 2 may comprise a barcode or colour identification tag which is preferably located within the housing of the laser device 1 when the delivery device 2 is connected to the laser device 1.

The delivery device 2 is preferably able to withstand Ethylene Oxide sterilisation and accordingly an encapsulated AC or RF identification tag 3 is particularly preferred.

The identification tag 3 may comprise a Read Only or a Read/Write device. The data held on the identification tag 3 may be pre-programmed onto the delivery device 2 during manufacture. If a Read/Write device is used the laser device 1 may update the information on the identification tag upon connection and may for example record the date and usage of the delivery device 2.

The information received by the laser device 1 is preferably displayed for the user on a display 4 which may be integral with the laser device 1. The information may be displayed, for example, as a series of messages and/or warning(s) based on the data exchanged.

The laser device 1 preferably automatically interrogates the delivery device 2 either upon connection of the delivery device 2 to the laser device 1 or upon switching the laser device 1 ON. Interrogation of the delivery device 2 at switch-on ensures that the laser device 1 detects whether a new delivery device 2 has been attached and whether or not the delivery device 2 is properly attached. The laser device 1 may also detect whether the delivery device 2 has been changed since the laser system 10 was last switched OFF. The laser device 1 preferably interrogates the delivery device 2 during or after completion of a self-test start-up procedure when the laser device 1 is first switched ON.

According to an embodiment an interrogating electromagnetic pulse is preferably transmitted from the reader of the laser device 1. The interrogating pulse may be of radio wave frequency.

The AC or RF identification tag or transponder 3 is preferably powered by an electromagnetic field generated by the reader. The antenna of the AC or RF identification tag or transponder 3 collects electromagnetic energy transmitted by the reader. When the power pulse has been received the AC or RF identification tag or transponder 3 transmits data to the reader using the energy received.

In an embodiment the RF or AC identification tag 3 may comprise either a conductively coupled RF or AC identification tag or a capacitively coupled RF or AC identification tag. The conductively coupled RF or AC identification tag may comprise a metal coil antenna powered by the magnetic field generated by the reader. A capacitively coupled RF or AC identification tag may comprise an antenna comprised of two plate electrodes. A capacitively coupled RF or AC identification tag is powered by an electric field generated by the reader, the field gradient causing a charge build up between the plates and thus a potential difference.

In accordance with a less preferred embodiment a laser system 10 may be provided with an electromagnetic tag which operates at a low frequency (typically between 70 Hz and 1 kHz).

Upon receiving the data from the delivery device 2 the laser device 1 may be activated if the data indicates that the delivery device 2 is in a usable condition. However, if the delivery device 2 is not usable, for example if its expiry date has passed or its usage limit has been exceeded, then the laser device 1 may prevent or restrict further operation and/or may preferably provide the user with one or more warning messages.

The laser device 1 may preferably receive information from the delivery device 2 which pre-configures the laser device 1 for use. For example, the laser device 1 may set the properties of the laser radiation to be transmitted to the delivery device. The settings may, for example, include the output power and/or pulse width and/or interval between pulses and/or the duration of the laser radiation. This may be particularly preferred in a medical laser device whereby the type of delivery device 2 and the settings for the laser device 1 may be specific to a particular treatment.

According to an embodiment a user may be allowed to override the laser system 10 to allow further limited use of the laser system 10, in for example emergency situations, when the laser device 1 has otherwise prevented use of the delivery device 2. The override may be limited to a single occasion and may require resetting by service personnel. Alternatively a secure tool may be provided for resetting the override function. The secure tool may, for example, comprise a dummy-delivery device comprising a tag 3, which transmits information to the laser device 1 and wherein the information resets the laser device 1. The secure tool may be limited to a single use. The display 4 of the laser device 1 may indicate when the override function has been used. A telephone link, serial connection, internet link or other connection may be provided for enabling/disabling the laser device 2 and for overriding the information exchange system.

In one preferred embodiment the override function may be limited to situations wherein the laser device 1 has not received information from the delivery device 2. Thus if the delivery device 2, for example, indicated to the laser device 1 that it was unsuitable for use since the expiry date of the delivery device 2 had passed then the user may not be allowed to override the system.

According to an embodiment the laser device 1 may only accept a delivery device 2 which transmits information to the laser device 1. According to another embodiment the laser device 1 may operate with any delivery device 2 but will interrogate the delivery device 2 for information before operation. In a preferred embodiment whether the laser device 1 only operates with a delivery device 2 which transmits information or with any delivery device may be selectable. The selection between these modes of operation may be restricted such that only trained service personnel may set the mode of operation of the laser device 1. For example, an internal switch may be provided or more preferably the system may be configured using a software engineering mode of the laser device 1. This may be accessible via a telephone link, serial connection or the internet. A secure tool, as previously described, may also be used to configure the system.

The delivery device 2 according to the preferred embodiment is preferably suitable for use with existing conventional laser devices which do not receive information from the delivery device 2.

The laser device 1 is preferably able to differentiate between separate delivery devices 2 such that the laser device 1 does not interrogate delivery devices other than the delivery device 2 actually attached to the laser device 1.

The device for interrogating the delivery device 1, such as an AC or RF identification tag reader or a bar code reader, may be installed within a conventional laser device. The receiving of information from the delivery device 2 to the laser device 1 is preferably software driven, controlled and switched. The modification of a conventional laser device such that it is operable in accordance with the preferred embodiment preferably would not have any significant effect on the overall size, weight or reliability of the laser device.

It will be appreciated that the above described embodiments are given by example only and that various modifications thereto may be made without departing from the scope of the invention.

What is claimed is:

1. A laser system comprising:
   a laser device for emitting laser radiation; and
   a delivery device comprising a read/write device for storing information, said delivery device adapted to connect, in use, to said laser device for delivering said laser radiation;
   wherein, in use, said laser device receives information from said delivery device, the information received from said delivery device is used to configure an operation of said laser device, and said laser device updates the information on said read/write device;
   wherein the information includes an indication of an expiry date of said delivery device.

2. The laser system of claim 1, wherein said delivery device comprises an optical fiber.

3. The laser system of claim 1, wherein said laser device comprises a SMA connector for receiving an optical fiber.

4. The laser system of claim 1, wherein said laser device comprises a detector for detecting the connection of said delivery device.

5. The laser system claim 4, wherein, in use, said laser device interrogates said delivery device after said detector indicates that said delivery device has been connected to said laser device.

6. The laser system of claim 1, wherein, in use, said laser device interrogates said delivery device.

7. The laser system of claim 6, wherein said laser device interrogates said delivery device in a contactless manner.

8. The laser system of claim 1, wherein said delivery device receives, in use, at least one of or both power and electromagnetic pulse.

9. The laser system of claim 1, wherein said delivery device receives, in use, one of AC or RF energy, stores said energy, and transmits back to said laser device at least one of or both data and information using said stored energy.

10. The laser system of claim 1, wherein said read/write device comprises at least one of or both an AC or RF identification tag and an AC or RF transponder.

11. The laser system of claim 10, wherein said at least one of or both the AC or RF identification tag and the AC or RF transponder is embedded within or provided on said delivery device.

12. The laser system of claim 10, wherein said at least one of or both the AC or RF identification tag and the AC or RF transponder comprises a conductively coupled AC or RF identification tag.

13. The laser system of claim 10, wherein said at least one of or both the AC or RF identification tag and the AC or RF transponder comprises a capacitively coupled AC or RF identification tag.

14. The laser system of claim 10, wherein said laser device comprises an AC or RF identification reader for reading said at least one of or both the AC or RF identification tag and the AC or RF transponder.

15. The laser system of claim 14, wherein said AC or RF identification reader comprises an antenna, a transceiver and a processor.

16. The laser system of claim 14, wherein, in use, said delivery device transmits or returns a signal to said AC or RF identification reader.

17. The laser system of claim 1, wherein said information indicates a type of said delivery device.

18. The laser system of claim 1, wherein said information indicates a state, usage, age and model of said delivery device.

19. The laser system of claim 1, wherein said information indicates at least one of or both an intended use and function of said delivery device.

20. The laser system of claim 1, wherein in a mode of operation said laser device prevents operation with said delivery device upon receiving information from said delivery device.

21. The laser system of claim 1, wherein in a mode of operation said laser device prevents operation with said delivery device if said laser device does not receive any information from said delivery device.

22. The laser system of claim 1, wherein in a mode of operation said laser device prevents operation with said delivery device if said laser device receives information from said delivery device and wherein said information indicates a predetermined parameter.

23. The laser system of claim 22, wherein said parameter indicates a usage of the delivery device.

24. The laser system of claim 22, wherein said parameter indicates a sterility of the delivery device.

25. The laser system of claim 22, wherein said parameter indicates a type of the delivery device.

26. The laser system of claim 1, wherein in a mode of operation said laser device receives information from said delivery device and sets a power of laser radiation to be transmitted to said delivery device.

27. The laser system of claim 1, wherein in a mode of operation said laser device receives information from said delivery device and sets a pulse width of laser radiation to be transmitted to said delivery device.

28. The laser system of claim 1, wherein in a mode of operation said laser device receives information from said delivery device and sets an interval between pluses of laser radiation to be transmitted to said delivery device.

29. The laser system of claim 1, wherein in a mode of operation said laser device receives information from said delivery device and sets the duration that laser radiation is to be transmitted to said said delivery device.

30. The laser system of claim 1, wherein said laser device may be at least one of or both enabled and disabled remotely.

31. The laser system of claim 30, wherein said laser device may be at least one of or both enabled and disabled via a telephone link, serial interface or internet.

32. The laser system of claim 1, wherein said laser device comprises a visual display, said display being adapted to provide a user with information received from said delivery device.

33. A method of operating a laser system comprising:

providing a laser device;

connecting a delivery device to said laser device, said delivery device including a read/write device for storing information, said laser device receiving information from said delivery device;

using the information received from said delivery device to configure an operation of said laser device; and updating the information on said read/write device;

wherein the information includes an indication of an expiry date of said delivery device.

\* \* \* \* \*